(12) United States Patent
Clark et al.

(10) Patent No.: US 11,007,007 B2
(45) Date of Patent: May 18, 2021

(54) SELF-CENTERING MULTIRAY ABLATION CATHETER

(71) Applicant: Biosense Webster (Israel) Ltd., Yokneam (IL)

(72) Inventors: Jeffrey Clark, Castaic, CA (US); John Ashton, Glendora, CA (US); Ryan Hoitink, Pasadena, CA (US); Jeffrey Schultz, Chino, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 887 days.

(21) Appl. No.: 14/881,576

(22) Filed: Oct. 13, 2015

(65) Prior Publication Data

US 2017/0100189 A1 Apr. 13, 2017

(51) Int. Cl.
*A61B 18/14* (2006.01)
*A61B 18/00* (2006.01)
(Continued)

(52) U.S. Cl.
CPC ............ *A61B 18/1492* (2013.01); *A61B 2017/00867* (2013.01); *A61B 2018/00029* (2013.01);
(Continued)

(58) Field of Classification Search
CPC ........ A61B 18/1492; A61B 2018/1465; A61B 2018/1405; A61B 2018/1407;
(Continued)

(56) References Cited

U.S. PATENT DOCUMENTS

| | | |
|---|---|---|
| 5,391,199 A | 2/1995 | Ben-Haim |
| 5,827,276 A | 10/1998 | Leveen et al. |

(Continued)

FOREIGN PATENT DOCUMENTS

| | | |
|---|---|---|
| EP | 0957794 | 11/1994 |
| EP | 1484011 | 12/2004 |

(Continued)

OTHER PUBLICATIONS

European Search Report and Written Opinion for European Application No. 16193439.3, dated Mar. 2, 2017.

*Primary Examiner* — Thomas A Giuliani
(74) *Attorney, Agent, or Firm* — Dergosits & Noah LLP; Todd A. Noah

(57) ABSTRACT

A catheter for ablating tissue is disclosed that has a self-centering multiray electrode assembly. The self-centering multiray electrode assembly may have a plurality of spines, each of which a preshaped, expanded configuration that curves to change an orientation of the spine from being directed towards the distal end of catheter body to being directed towards the proximal end of the catheter body. The ablation electrodes engage ostial tissue when a maximal outer diameter of the self-centering multiray electrode assembly is engaged with an inner diameter of a vessel. The compliance of each spine may vary along its length. When the self-centering multiray electrode assembly is engaged within a vessel, the ablation electrodes are brought into contact with tissue and may be used to form lesions in a circumferential path around the vessel.

20 Claims, 6 Drawing Sheets

(51) Int. Cl.
*A61B 34/20* (2016.01)
*A61B 17/00* (2006.01)

(52) U.S. Cl.
CPC ............... *A61B 2018/00214* (2013.01); *A61B 2018/00279* (2013.01); *A61B 2018/00375* (2013.01); *A61B 2018/00577* (2013.01); *A61B 2018/00755* (2013.01); *A61B 2018/00821* (2013.01); *A61B 2018/1422* (2013.01); *A61B 2018/1467* (2013.01); *A61B 2018/1475* (2013.01); *A61B 2034/2051* (2016.02); *A61B 2218/002* (2013.01)

(58) Field of Classification Search
CPC .. A61B 2018/1435; A61B 2018/00375; A61B 2018/00273; A61B 2018/00214; A61B 2018/00267; A61B 2018/1475; A61B 2018/00279; A61B 2018/1467; A61B 2018/1422; A61B 2017/00867
USPC ................................................ 606/41, 47, 49
See application file for complete search history.

(56) References Cited

U.S. PATENT DOCUMENTS

| | | | |
|---|---|---|---|
| 5,855,576 A | 1/1999 | Leveen et al. | |
| 5,868,740 A | 2/1999 | Leveen et al. | |
| 6,064,905 A | 5/2000 | Webster, Jr. | |
| 6,239,724 B1 | 5/2001 | Doron et al. | |
| 6,332,089 B1 | 12/2001 | Acker et al. | |
| 6,484,118 B1 | 11/2002 | Govari | |
| 6,575,967 B1 | 6/2003 | Leveen et al. | |
| 6,618,612 B1 | 9/2003 | Acker et al. | |
| 6,690,963 B2 | 2/2004 | Ben-Haim | |
| 8,348,940 B2 | 1/2013 | Behl et al. | |
| 8,663,190 B2 | 3/2014 | Fischell et al. | |
| 2002/0022864 A1 | 2/2002 | Mahvi et al. | |
| 2002/0065455 A1 | 5/2002 | Ben-Haim et al. | |
| 2003/0093072 A1 | 5/2003 | Friedman | |
| 2003/0120150 A1 | 6/2003 | Govari | |
| 2003/0208199 A1 | 11/2003 | Keane | |
| 2004/0068178 A1 | 4/2004 | Govari | |
| 2006/0095030 A1* | 5/2006 | Avitall | A61B 18/1492 606/41 |
| 2009/0216221 A1* | 8/2009 | Davis | A61B 18/082 606/33 |
| 2012/0271277 A1 | 10/2012 | Fischell et al. | |
| 2013/0304047 A1* | 11/2013 | Grunewald | A61M 25/09 606/14 |
| 2014/0018788 A1* | 1/2014 | Engelman | A61B 18/18 606/33 |
| 2014/0046298 A1 | 2/2014 | Fischell et al. | |
| 2017/0100187 A1* | 4/2017 | Basu | A61B 18/02 |

FOREIGN PATENT DOCUMENTS

| | | |
|---|---|---|
| EP | 1639957 A1 | 3/2006 |
| EP | 2540245 | 1/2013 |
| EP | 2662048 | 11/2013 |
| WO | 96/05768 A1 | 2/1996 |
| WO | 09/094588 | 7/2009 |

* cited by examiner

SELF-CENTERING MULTIRAY ABLATION CATHETER

FIELD OF THE PRESENT DISCLOSURE

This invention relates to electrophysiologic (EP) catheters, in particular, EP catheters for ablating tissue in the heart.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region along the pulmonary veins of the left atrium and in the superior pulmonary veins. In this condition, after unwanted signals are generated in the pulmonary veins or conducted through the pulmonary veins from other sources, they are conducted into the left atrium where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is sometimes possible to cease or modify the propagation of unwanted electrical signals from one portion of the heart to another. The ablation process destroys the unwanted electrical pathways by formation of non-conducting lesions. An example of such ablation procedures is termed pulmonary vein isolation, and involves the ablation of tissue in the area adjacent the junction of the pulmonary veins and the left atrium. The resulting lesion(s) may isolate irregular electrical signals originating in the area from spreading through the rest of the atrium and disrupting the patient's heart beat.

For these and other applications, conventional practice may involve positioning an ablation catheter adjacent target regions to deliver sufficient energy to form the non-conducting lesions in a circumferential path around a vessel such as a pulmonary vein. Accordingly, it would be desirable to provide a catheter and a technique for facilitating electrical isolation of a source of unwanted signals within such a vessel. Likewise, it would be desirable it reduce or avoid the need to reposition a catheter while performing the ablation procedure. As will be described in the following materials, this disclosure satisfies these and other needs.

SUMMARY

The present disclosure is directed to a catheter with an elongated catheter body having proximal and distal ends and a self-centering multiray electrode assembly composed of a plurality of spines connected at one end with each spine having at least one ablation electrode. The spines have a preshaped, expanded configuration that curves to change an orientation of the spine from being directed towards the distal end of catheter body to being directed towards the proximal end of the catheter body.

In one aspect, each spine may include a strut for imparting the preshaped configuration. The strut may be made from a shape memory material.

In one aspect, the compliance of the spine may vary along its length. For example, each spine may have a strut with a varying cross sectional area.

In one aspect, each spine may have a first region that curves to change the orientation of the spine from being directed towards the distal end of catheter body at a first end of the first curved region to being directed towards the proximal end of the catheter body at a second end of the first curved region. The self-centering multiray electrode assembly may have a maximal outer diameter within the first curved region at an intermediate location of the first curved region. For example, the maximal outer diameter of the first curved region may be between 7.5 and 15 mm. The ablation electrodes may be configured to engage ostial tissue when the maximal outer diameter of the self-centering multiray electrode assembly is engaged with an inner diameter of a vessel.

In one aspect, each spine may also have a second region oriented towards the proximal end of the catheter body, with a first end that starts at the second end of the first curved region. The first region may be relatively less compliant than the second region. The second region may be curved in an opposite direction from the first region so that a second end of the second region flares radially outward from a longitudinal axis of the catheter body. Alternatively, the second region may cross a longitudinal axis of the catheter body so that a second end of the second region flares radially outward from the longitudinal axis of the catheter body. In such embodiments, an inward radial force applied to the first region may be translated to an outward radial force at the second region.

In one aspect, each spine may also have a third region that starts at the second end of the second region with a longitudinally oriented curve to form an atraumatic tip. Alternatively, each spine may have a third region that starts at the second end of the second region with a circumferentially oriented curve. The third region may have a plurality of ablation electrodes.

In one aspect, the self-centering multiray electrode assembly may have at least three spines.

This disclosure also includes a method for treatment that includes providing a catheter with an elongated catheter body having proximal and distal ends and a self-centering multiray electrode assembly with a plurality of spines connected at one end and each spine comprising at least one ablation electrode, wherein each spine has a preshaped, expanded configuration that curves to change an orientation of the spine from being directed towards the distal end of catheter body to being directed towards the proximal end of the catheter body, positioning the distal end of the catheter at a desired region of the heart, engaging the self-centering multiray electrode assembly within an ostium of a vessel to bring ablation electrodes into contact with tissue and delivering radio frequency energy to the ablation electrodes to form lesions.

In one aspect, the lesions may be formed in a circumferential path around the vessel.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
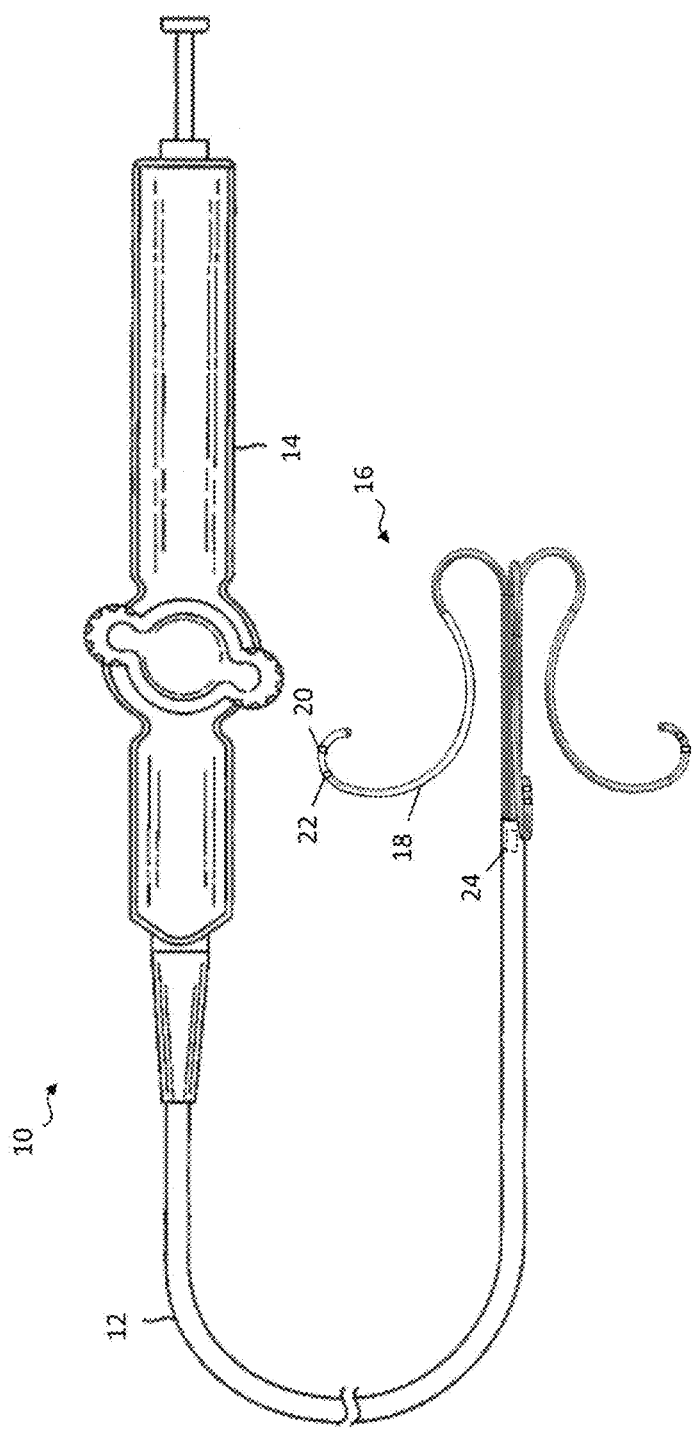
FIG. 1 is a schematic elevational view of a catheter with a self-centering multiray electrode assembly, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Certain types of electrical activity within a heart chamber are not cyclical. Examples include atrial fibrillation and other asynchronous conditions that may result from undesired signals originating in the pulmonary veins. As noted, RF energy may be delivered to selected treatment areas with a goal of isolating the source of irregular electrical signals by blocking electrical conduction. Important clinical therapies for pulmonary vein isolation include RF ablation via focal or multielectrode catheters.

Focal ablations using unipolar devices benefit from targeted delivery of RF energy along with localized feedback of catheter placement, both spatially and with respect to tissue engagement. However, focal ablation procedures typically involve relative long procedure times as a result of the physician needing to stich a series of "quantized" RF ablation into a continuous circumferential block which surrounds the osteum of the targeted vein. Additionally, the use of a focal unipolar electrode requires substantial physician skill levels augmented with peripheral navigation systems in order to accurately and reliably position the electrode sequentially along the desired circumferential path.

Correspondingly, use of a multielectrode device seeks to capitalize on the somewhat predictable anatomical structure of the pulmonary vein in order to place an array of unipolar electrodes in a fixed circumferential path around the inner diameter of a targeted vein. RF energy may then be delivered simultaneously to the electrode array, thereby theoretically reducing the time for therapeutic delivery by creating the requisite ablations in parallel. In practice, it has been observed that it may be difficult to achieve good tissue contact around the entire circumference due to the variable topography of the osteum of a pulmonary vein. Suboptimal tissue engagement results in ineffective energy delivery at some electrode sites and necessitates additional device placements, or in some cases, lesion closure via unipolar ablations from a focal type device. It may also be difficult to properly orient the electrode array by aligning the center normal axis of the array with the center axis of pulmonary vein for a variety of reasons, including the limited space in the left atrium, the variable anatomy of the pulmonary vein, and the finite kinematic properties of the device deploying the electrode array.

As will be described herein, this disclosure is directed to a catheter having a self-centering multiray electrode assembly. The electrode assembly features multiple spines having a preshaped expanded configuration that facilitates deployment in a desired orientation with respect to a vessel, such as a pulmonary vein. Similarly, the preshaped expanded configuration may also help ensure sufficient contact between the ablation electrodes and the target tissue to allow proper lesion formation. Further, the spines may exhibit variable compliance characteristics along their length to provide a desired amount of force to hold the ablation electrodes in contact with the tissue.

To help illustrate aspects of this disclosure, an exemplary embodiment of a ablation catheter with a self-centering multiray electrode assembly is shown schematically in FIG. 1. Catheter 10 comprises an elongated catheter body 12 having proximal and distal ends and a control handle 14 at the proximal end of the catheter body, with a self-centering multiray electrode assembly 16 with multiple spines 18 radiating outwards in a multiray configuration. Each spine 18 may have a preshaped expanded configuration as described below that is assumed when the spine is unconstrained. Self-centering multiray electrode assembly 16 may be a discrete element that is joined to catheter body 12 or may comprise an extension of catheter body 12. Self-centering multiray electrode assembly 16 may be of a known fixed length, and comprises material that preferably is twistable but not stretchable when subjected to typical forces. Spines 18 may be sufficiently resilient so as to assume the preshaped configuration but also may be placed in a collapsed configuration in which they are straightened and aligned with the longitudinal axis of catheter body 12. By employing a plurality of spines 18, such as at least two, self-centering multiray electrode assembly 16 may be stabilized within a patient's vessel. Further, using three or more spines 18 may cause the central axis of self-centering multiray electrode assembly 16 to assume a position that is collinear with the central axis of the vessel in which it is deployed. Different numbers of spines 18 may be employed to achieve a desired stability of self-centering multiray electrode assembly 16 when deployed and/or to bring a desired number of electrodes 20 into contact with tissue to form the circumferential lesion. For example, four, five, six or even more spines 18 may be employed depending on the embodiment.

Each spine 18 may carry one or more electrodes 20 generally positioned near the distal end of the spines at locations expected to be in contact with tissue when self-centering multiray electrode assembly 16 is deployed within a patient's heart. For example, electrodes 20 may be unipolar ablation electrodes. As desired, electrodes 20 may be configured to preferentially deliver RF energy in a specific radial direction, such as towards the tissue. In some embodiments, electrodes 20 may have perforations to allow for the delivery of irrigation fluid to the treatment site to help manage the temperature of the tissue be ablated. During delivery of RF current to each electrode 20, heating of the tissue occurs due to its electrical resistance. Heating the tissue causes cellular destruction in the target tissue that results in the formation of the non-conducting lesion that is intended to disrupt the influence of aberrant electrical signals. However, overheating the tissue may cause the undesirable formation of char and coagulum or may result in steam pops when liquid is heated beyond its boiling point, which in turn may create craters or perforations in the heart tissue. Correspondingly, irrigation at the ablation site may provide benefits including cooling of the electrode and tissue to prevent overheating of tissue. Additionally, spines 18 may also have thermocouple 22 or other suitable temperature sensor to assess tissue temperature during an ablation procedure for avoiding such adverse occurrences and to help adjust the flow of irrigation fluid to prevent or minimize overheating. Thus, when self-centering multiray electrode assembly 16 is positioned within the ostium of a vessel such as a pulmonary vein, spines 18 may bring electrodes 20 into contact with tissue at multiple locations. Each spine 18 may independently conform to the anatomy of the osteum to provide a desired degree of contact. Delivering energy to electrodes 20 may then simultaneously create multiple lesions in a circumferential path around the inner diameter of the vessel.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner. In some embodiments, catheter body 12 may be steerable and/or deflectable using any suitable technique, which are known to those of ordinary skill in the art. The outer diameter of the catheter body 12 is not critical, but generally should be as small as possible and may be no more than about 10 french depending on the desired application. For example, for use in ablation for isolation of a pulmonary vein, catheter body 12 may have an outer diameter of about 7 to 7.5 french. Likewise the thickness of the outer wall is not critical, but may be thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference. In some embodiments, catheter body 12 and/or self-centering multiray electrode assembly 16 may include one or more single- or multi-coil position sensors, such as sensors 24 located at the base of self-centering multiray electrode assembly 16 where it joins catheter body 12. As described below, such position sensors may be used to help determine the position and/or orientation of self-centering multiray electrode assembly 16 within the patient.

Figure 2:
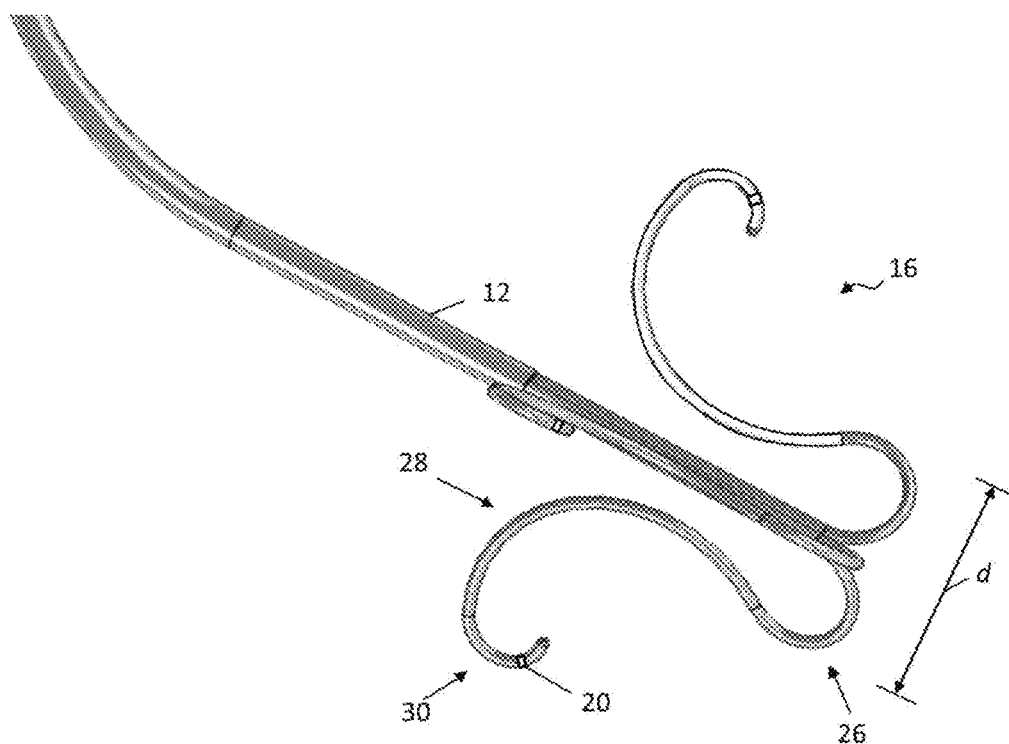
FIG. 2 is a more detailed schematic view of the self-centering multiray electrode assembly of FIG. 1, according to one embodiment.

Further details regarding self-centering multiray electrode assembly 16 are shown in FIG. 2 which depicts self-centering multiray electrode assembly 16 in its preshaped, expanded configuration in which each spine curves to change orientation from being directed towards the distal end of catheter 10 to being directed towards the proximal end. For example, each spine may have a first region 26 and a second region 28 when unconstrained. In this embodiment, first region 26 may be curved and exhibit a total curvature of approximately 180° or more, so that the orientation of first region 26 transitions from being directed towards the distal end of catheter 10 to being directed towards the proximal end of catheter 10. Second region 28 may have curvature with an opposite orientation to that of first region 26, so that second region 28 flares radially outward. For example, the curvature over first region 26 and second region 28 may have a total curvature in the range of approximately 80-100°, so that the distal end of second region 28 is generally perpendicular to the longitudinal axis of catheter body 12. Each spine 18 may further have a third region 30. In this embodiment, third region 30 may have a curvature with the same orientation as second region 28 of greater than approximately 90° and up to approximately 180° or more to create an atraumatic distal end for each spine 18. First region 26, second region 28 and third region 30 may all be substantially coplanar and lie in the same plane as the longitudinal axis of catheter body 12, such that each region may be considered longitudinally oriented. Electrodes 20 may be located in third region 28 at a position or positions expected to be in contact with tissue when self-centering multiray electrode assembly 16 is deployed.

The curvature of first region 26 of each spine 18 may define a maximal outer diameter d of the first region as indicated, which may be sized to correspond to the inner diameter of the vessel in which self-centering multiray electrode assembly 16 is to be deployed. For example, for pulmonary vein applications, the maximal outer diameter may be in the range of approximately 7.5 to 15 mm. By selecting an appropriate diameter d, the first region 26 of each spine 18 may engage the tissue forming the vessel wall to stabilize self-centering multiray electrode assembly 16 within the vessel. Further, the symmetrical configuration of spines 18 serve to center self-centering multiray electrode assembly 16 within the vessel, aligning the center normal axis of the assembly with the center axis of vessel. As noted, the preshaped configuration of second region 28 flares radially outward, which helps maintain engagement between the vessel wall and electrodes 20.

Figure 3:
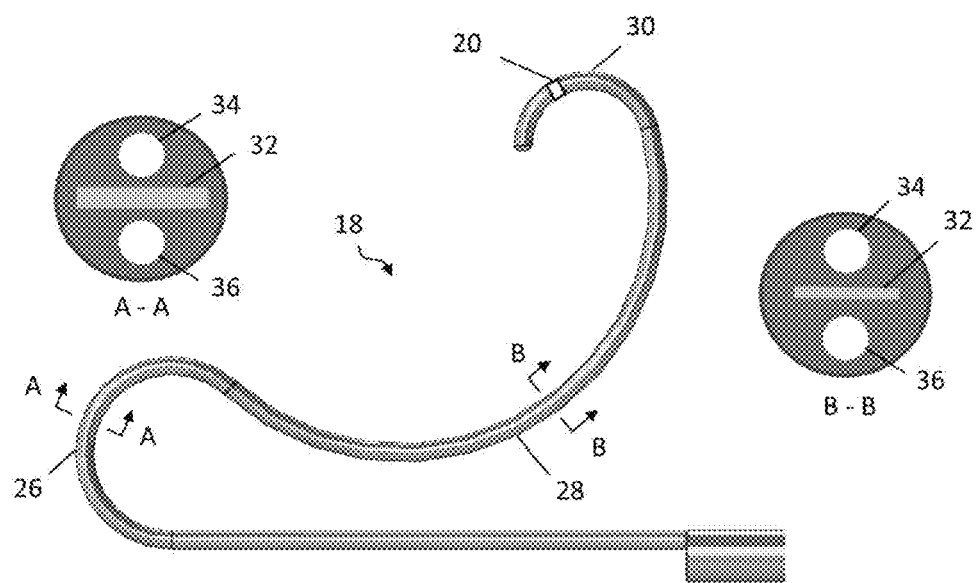
FIG. 3 schematically illustrates one spine of the self-centering multiray electrode assembly of FIG. 2, with cross sections showing varying compliance, according to one embodiment.

Additionally, the compliance of one or more regions of each spine 18 may be varied with respect to other regions to tailor the kinematics of self-centering multiray electrode assembly 16 as desired. For example, FIG. 3 shows one spine 18 with cross sections A-A and B-B taken at the indicated locations in first region 26 and second region 28, respectively. A structural member, such as strut 32, may be embedded within a polymeric material forming spine 18 to help assume the preshaped configuration. For example, strut 32 may be formed from a suitable shape memory alloy, such as Nitinol or other nickel-titanium alloys, which assumes a remembered shape when heated to physiological temperatures. Further, strut 32 may be used to impart varying degrees of compliance to one or more regions of strut 18. For example, it may be desirable for first region 26 to exhibit relatively less compliance to facilitate the centering function described above. As such, strut 32 may have a relatively increased cross sectional area in first region 26 as shown in section A-A. Likewise, second region 28 may exhibit relatively greater compliance to facilitate conformation to the anatomy of the vessel and to create engagement between the vessel wall tissue and electrode 20 with a desired amount of contact force. Correspondingly, strut 32 may have a relatively decreased cross sectional area in second region 28 as shown in section B-B. Either or both of width and thickness may be varied to impart the amount of compliance desired. Alternatively or in addition, any other technique for altering the compliance of spine 18 at different regions may be employed, such as by altering the type or characteristics of the polymeric material forming the spine. Each spine 18 may also have any suitable number of lumens, such as lumens 34 and 36 in this embodiment, which may be used as irrigation lumens for delivery of fluid to electrodes 20 or for accommodating leads for electrodes 20, thermocouple 22, and other sensors such as position sensors or for other purposes.

As noted, strut 32 may be formed from a shape memory material in some embodiments. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°–60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, self-centering multiray electrode assembly 16 may have a three dimensional shape that can be easily collapsed to be fed into a guiding sheath and then readily returned to its expanded shape memory configuration upon delivery to the desired region of the patient upon removal of the guiding sheath.

Figure 4:
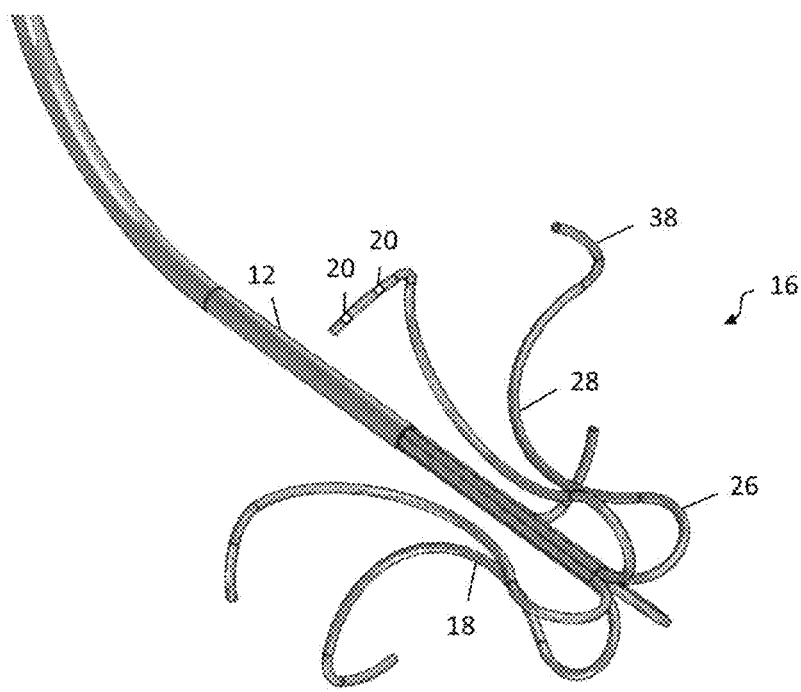
FIG. 4 is a schematic view of a self-centering multiray electrode assembly having a circumferentially oriented region, according to one embodiment.

Another embodiment of this disclosure is shown in FIG. 4, with self-centering multiray electrode assembly 16 implemented using five spines 18. As will be appreciated, the preshaped expanded configuration of this embodiment shares similarities with the embodiment shown in FIG. 3, with first region 26 and second region 28 as described above. However, while first region 26, second region 28 and the longitudinal axis of catheter body 12 are all generally coplanar as above, third region 38 may be circumferentially oriented instead and lie in a plane that intersects the plane of first region 26, second region 28 and the longitudinal axis of catheter body 12. In one aspect, this plane may be substantially perpendicular, although other angles may be employed as desired. Further, since third region 38 is circumferentially oriented, it may be desirable to use a plurality of electrodes 20 per spine 18. Given the orientation of third region 38, such electrodes 20 may be substantially on a circumferential path around the interior wall of the vessel, allowing for the creation of a more complete circumferential lesion. Again, the relative compliance of any region of spines 18, such as first region 26, second region 28 and third region 38 may be adjusted to improve performance of self-centering multiray electrode assembly 16.

Figure 5:
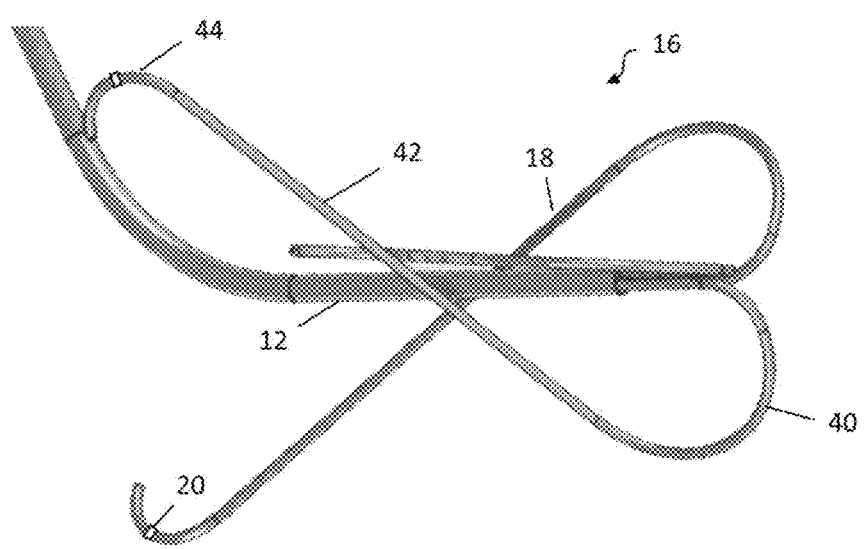
FIG. 5 is a schematic view of another configuration of a self-centering multiray electrode assembly, according to one embodiment.

A still further embodiment of self-centering multiray electrode assembly 16 is shown in FIG. 5. Here, each spine 18 may have a first region 40 that is curved and may exhibit a total curvature of greater than 180° and a second region 42 with a relatively straight shape, so that spine 18 crosses the longitudinal axis of catheter body 12 while being oriented towards the proximal end of catheter 10. Alternatively, first region 40 may have less curvature, and second region 42 may have some curvature in the same direction, again so that spine 18 crosses the longitudinal axis of catheter body 12. The first regions 40 of spines 18 may form a maximal outer diameter as described above that may be tailored with respect to the inner diameter of the vessel in which self-centering multiray electrode assembly 16 will be deployed. Each spine 18 may further have a third region 44, similar to the embodiment of FIG. 2, with a longitudinally oriented curvature directed radially outward of greater than approximately 90° and up to approximately 180° or more to create an atraumatic distal end for each spine 18. Similarly, first region 40, second region 42 and third region 44 may all be substantially coplanar and lie in the same plane as the longitudinal axis of catheter body 12.

In this embodiment, it will be appreciated that the force exerted by the vessel wall tissue against first region 40 will tend to be transmitted by the lever arm formed by second region 42, urging electrodes 20 into greater contact with the vessel wall tissue and helping self-centering multiray electrode assembly 16 conform to variations in vessel anatomy. Using the techniques noted above, the relative compliance of any region of spines 18, such as first region 40, second region 42 and third region 44 may be adjusted to improve performance of self-centering multiray electrode assembly 16. For example, it may be desirable for first region 40 to be relatively less compliant and for second region 42 to be relatively more compliant.

Figure 6:
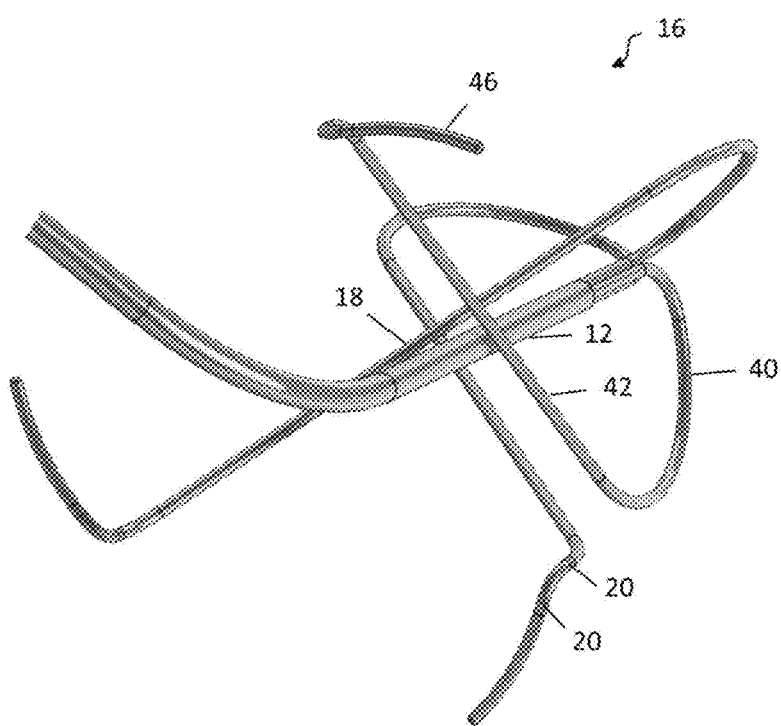
FIG. 6 is a schematic view of yet another self-centering multiray electrode assembly having a circumferentially oriented region, according to one embodiment.

Yet another embodiment of self-centering multiray electrode assembly 16 is shown in FIG. 6, with a configuration similar to that shown in FIG. 5. First region 40 and/or second region 42 may have curvatures that cooperate to cause spine 18 to cross the longitudinal axis of catheter body 12 as described above. In this embodiment, third region 48 may be oriented circumferentially rather than longitudinally so that it is not coplanar with first region 40, second region 42 and the longitudinal axis of catheter body 12. In a further aspect, each spine 18 may have multiple electrodes 20. As shown, one or more electrodes may be on a circumferentially oriented portion of spine 18 and one or more electrodes may be on a longitudinally oriented portion of spine 18. By presenting electrodes 20 at varying angles, the probability of achieving suitable contact with tissue for at least one of the electrodes may be increased.

Figure 7:
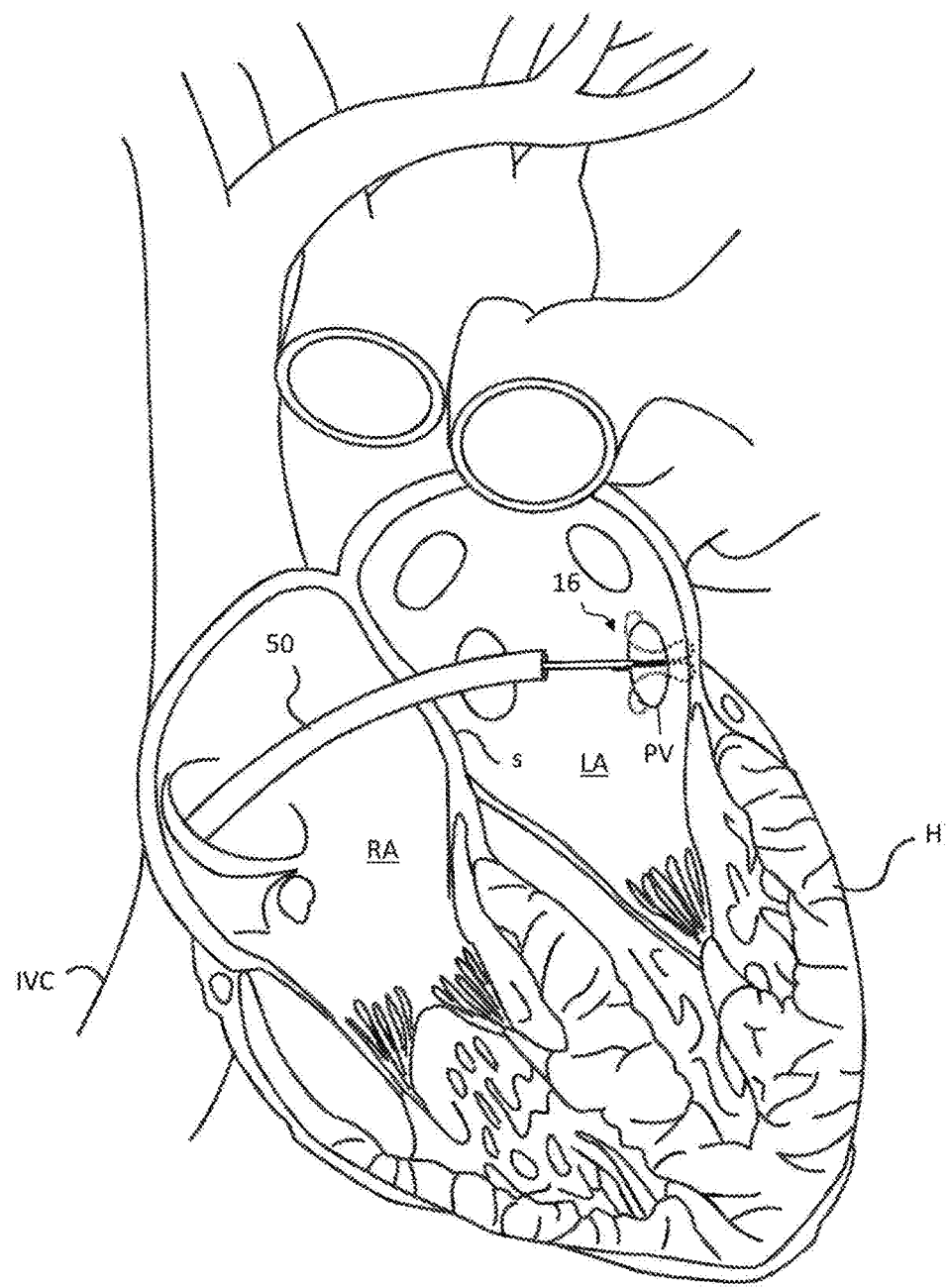
FIG. 7 is a schematic view of a self-centering multiray electrode assembly deployed within a patient's heart, according to one embodiment.

In one aspect, an electrophysiologist may introduce a guiding sheath, guidewire and dilator into the patient, as is generally known in the art. As an example, a guiding sheath for use in connection with the inventive catheter is an appropriately-sized PREFACE™ Braided Guiding Sheath (commercially available from Biosense Webster, Inc., Diamond Bar, Calif.). The guidewire is inserted, the dilator is removed, and the catheter is introduced through the guiding sheath whereby the guidewire lumen in the expander permits the catheter to pass over the guidewire. In one exemplary procedure as depicted in FIG. 7, the catheter is first introduced to the patient's heart (H) through the right atrium (RA) via the inferior vena cava (IVC), where it passes through the septum (S) in order to reach the left atrium (LA).

As will be appreciated, self-centering multiray electrode assembly 16 may be deflected into a straightened configuration and constrained within guiding sheath 50 to allow catheter 10 to be passed through the patient's vasculature to the desired location. Once the distal end of the catheter reaches the desired location, e.g., the left atrium, guiding sheath 50 is withdrawn to expose the self-centering multiray electrode assembly 16, where it assumes its preshaped expanded configuration. With the self-centering multiray electrode assembly 16 then positioned and stabilized in the ostium of a pulmonary vein (PV), electrodes 20 contact the ostial tissue and may be used to ablate tissue in a circumferential path around the inner vessel wall. Depending upon the number of spines 18 and the number electrodes being employed, a substantially complete circumferential lesion may be formed simultaneously in some embodiments. In other embodiments, catheter 10 may be rotated after forming a first set of lesions, so that electrodes 20 come into contact with new areas of tissue along the circumferential path and the delivery of ablation energy may then be repeated. The sequence of rotation and delivery of energy may be repeated as warranted. Formation of a substantially complete lesion around the circumference of the vessel may electrically isolate the source of abnormal signals as described above.

Figure 8:
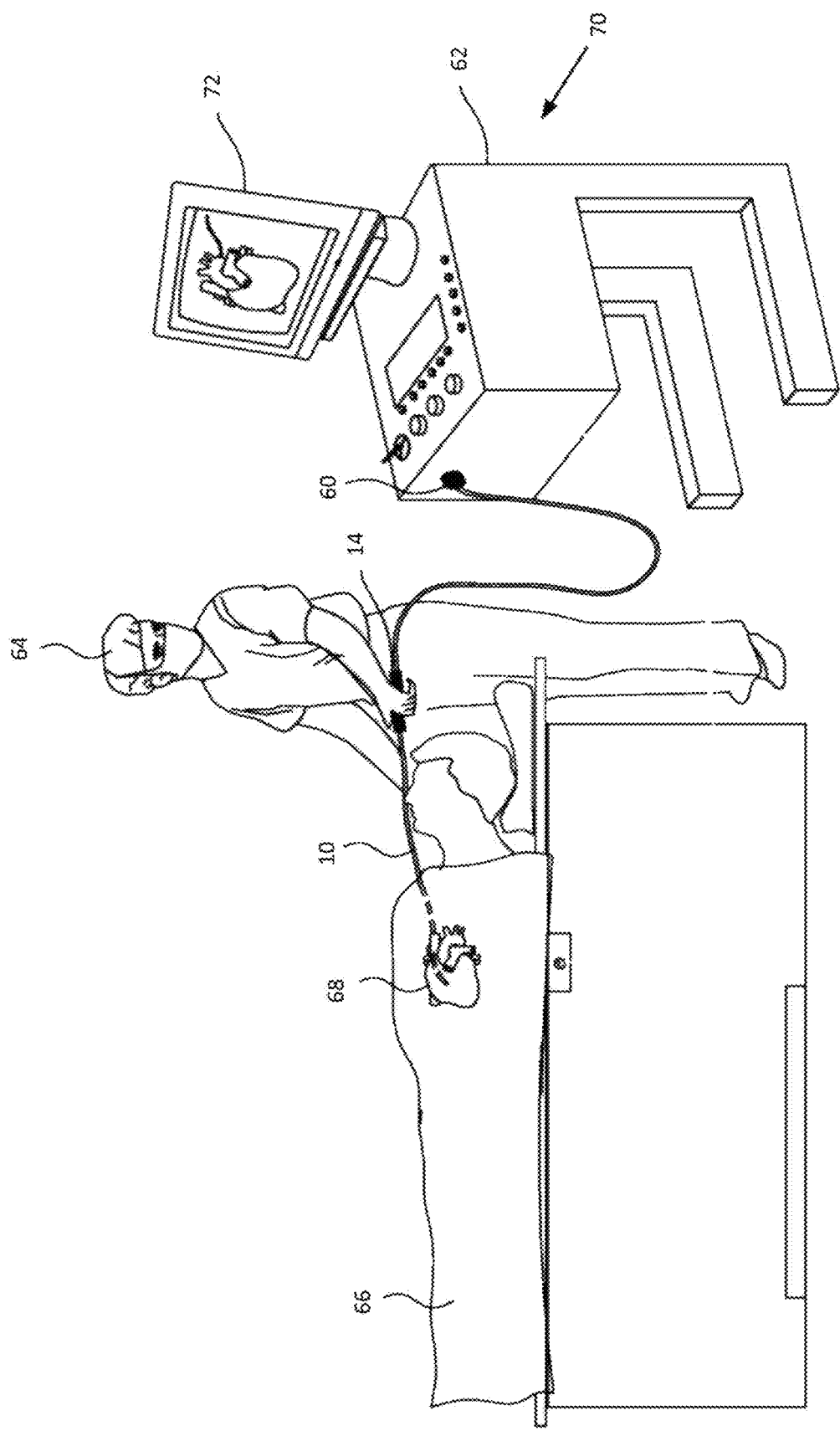
FIG. 8 is a schematic illustration of an invasive medical procedure using a self-centering multiray electrode assembly, according to one embodiment.

To help illustrate use of the self-centering multiray electrode assembly 16, FIG. 8 is a schematic depiction of an invasive medical procedure, according to an embodiment of the present invention. Catheter 10, with the self-centering multiray electrode assembly 16 (not shown in this view) at the distal end may have a connector 60 at the proximal end for coupling the leads of the electrodes and sensors (not shown in this view) to a console 62 for recording and analyzing the signals they detect as well as for supplying ablating energy. An electrophysiologist 64 may insert the catheter 10 into a patient 66 in order to acquire electropotential signals from the heart 68 of the patient. The electrophysiologist 64 uses the control handle 14 attached to the catheter in order to perform the insertion. Console 62 may include a processing unit 70 which analyzes the received signals, and which may present results of the analysis on a display 72 attached to the console. The results are typically in the form of a map, numerical displays, and/or graphs derived from the signals. Processing unit 70 may also control the delivery of energy to electrode 24 for creating one or more lesions. The electrophysiologist 64 may perform the operations described above to create a substantially complete circumferential lesion.

Further, the processing unit 70 may also receive signals from position sensors, such as sensor 24 (not shown in this view). As noted, the sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 70 to determine the position, (e.g., the location and orientation) of the distal end of catheter 10 within the heart cavity. The electrophysiologist may then view the position of the self-centering multiray electrode assembly 16 on an image the patient's heart on the display 72. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally with respect to self-centering multiray electrode assembly 16. The coordinates of the distal sensor relative to the proximal sensor may be determined and, with other known information pertaining to the configuration of self-centering multiray electrode assembly 16, used to find the positions of each of the electrodes 20.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising an elongated catheter body having proximal and distal ends and a self-centering multiray electrode assembly with a plurality of spines connected at one end and each spine comprising at least one ablation electrode, each spine having: (i) a preshaped, expanded configuration that curves to change an orientation of the spine from being directed towards the distal end of catheter body to being directed towards the proximal end of the catheter body, (ii) a first region that curves to change the orientation of the spine from being directed towards the distal end of catheter body at a first end of the first curved region to being directed towards the proximal end of the catheter body at a second end of the first curved region, (iii) a second region oriented towards the proximal end of the catheter body, with a first end that starts at the second end of the first curved region, the second region having a curvature that changes the orientation of the spine and is different than the curvature of the first region, (iv) a third region that starts at a second end of the second region and is curved along its length to change the orientation of the spine, the curvature bending away from a longitudinal axis of the catheter body and being different than the second region curvature, and (v) an embedded strut, each strut being centrally located along a longitudinal axis of each of the spines and having a varying cross-sectional area along a length of the spine, wherein the first region has a first cross-sectional area of the strut that transitions to a second cross-sectional area of the strut within the second region, the first cross-sectional area dimension being greater than the second cross-sectional area dimension.

2. The catheter of claim 1, wherein each spine comprises the strut for imparting the preshaped configuration.

3. The catheter of claim 2, wherein the strut comprises a shape memory material.

4. The catheter of claim 1, wherein each spine has a length and wherein compliance of the spine varies along the length.

5. The catheter of claim 1, wherein the self-centering multiray electrode assembly has a maximal outer diameter within the first curved region at an intermediate location of the first curved region.

6. The catheter of claim 5, wherein the maximal outer diameter of the first curved region is between 7.5 and 15 mm.

7. The catheter of claim 5, wherein the ablation electrodes are configured to engage ostial tissue when the maximal outer diameter of the self-centering multiray electrode assembly is engaged with an inner diameter of a vessel.

8. The catheter of claim 1, wherein the first region is relatively less compliant than the second region.

9. The catheter of claim 1, wherein the second end of the second region flares radially outward from the longitudinal axis of the catheter body.

10. The catheter of claim 1, wherein the second region crosses the longitudinal axis of the catheter body so that the second end of the second region flares radially outward from the longitudinal axis of the catheter body.

11. The catheter of claim 10, wherein an inward radial force applied to the first region is translated to an outward radial force at the second region.

12. The catheter of claim 1, wherein the third region of each spine comprises an atraumatic tip.

13. The catheter of claim 1, wherein the third region of each spine comprises a circumferentially oriented curve.

14. The catheter of claim 13, wherein the third region comprises a plurality of ablation electrodes.

15. The catheter of claim 1, wherein the self-centering multiray electrode assembly comprises at least three spines.

16. A method for treatment comprising: providing a catheter with an elongated catheter body having proximal and distal ends and a self-centering multiray electrode assembly with a plurality of spines connected at one end and each spine comprising at least one ablation electrode, each spine having: a preshaped, expanded configuration that curves to change an orientation of the spine from being directed towards the distal end of catheter body to being directed towards the proximal end of the catheter body, a first region that curves to change the orientation of the spine from being directed towards the distal end of catheter body at a first end of the first curved region to being directed towards the proximal end of the catheter body at a second end of the first curved region, a second region oriented towards the proximal end of the catheter body, with a first end that starts at the second end of the first curved region, the second region having a curvature that changes the orientation of the spine and is different than the curvature of the first region, a third region that starts at a second end of the second region and is curved along its length to change the orientation of the spine, the curvature bending away from a longitudinal axis of the catheter body and being different than the second region curvature, and an embedded strut, each strut being centrally located along a longitudinal axis of each of the spines and having a varying cross-sectional area along a length of the spine, wherein the first region has a first cross-sectional area of the strut that transitions to a second cross-sectional area of the strut within the second region, the first cross-sectional area dimension being greater than the second cross-sectional area dimension, and; positioning the distal end of the catheter at a desired region of a heart; engaging the self-centering multiray electrode assembly within an ostium of a vessel to bring the ablation electrodes into contact with tissue; and delivering radio frequency energy to the ablation electrodes to form lesions.

17. The method of claim 16, further comprising forming lesions in a circumferential path around the vessel.

18. The method of claim 16, wherein the self-centering multi ray electrode assembly has a maximal outer diameter within the first curved region at an intermediate location of the first curved region.

19. The method of claim 18, wherein the ablation electrodes are configured to engage the ostial tissue when the maximal outer diameter of the self-centering multi ray electrode assembly is engaged with an inner diameter of the vessel.

20. The method of claim 16, wherein the self-centering multi ray electrode assembly comprises at least three spines.

* * * * *